(12) United States Patent
Markowitz et al.

(10) Patent No.: US 7,315,759 B2
(45) Date of Patent: Jan. 1, 2008

(54) IMPLANTABLE MEDICAL DEVICE WITH CIRCULATION DELAY MEASUREMENT AND THERAPY CONTROL

(75) Inventors: H. Toby Markowitz, Roseville, MN (US); Pooja Mehta, Hanover Park, IL (US); Chad T. Giese, St. Paul, MN (US); Mark K. Erickson, Brooklyn Park, MN (US); Yong K. Cho, Maple Grove, MN (US); Marina Jovanovic, Minneapolis, MN (US); Sameh Sowelam, Maple Grove, MN (US)

(73) Assignee: Medtronic, Inc., Minneapolis, MN (US)

( * ) Notice: Subject to any disclaimer, the term of this patent is extended or adjusted under 35 U.S.C. 154(b) by 396 days.

(21) Appl. No.: 10/945,639

(22) Filed: Sep. 21, 2004

(65) Prior Publication Data

US 2005/0251218 A1 Nov. 10, 2005

Related U.S. Application Data

(60) Provisional application No. 60/569,434, filed on May 7, 2004.

(51) Int. Cl.
*A61N 1/08* (2006.01)
(52) U.S. Cl. ...................................................... 607/18
(58) Field of Classification Search .................. 607/20, 607/17, 42, 6, 18, 22, 62; 600/323–325, 600/529, 484; 128/204.23
See application file for complete search history.

(56) References Cited

U.S. PATENT DOCUMENTS 5,146,918 A * 9/1992 Kallok et al. .................. 607/2
2004/0220629 A1* 11/2004 Kamath et al. ................ 607/6

* cited by examiner

*Primary Examiner*—Angela D. Sykes
*Assistant Examiner*—Terri Lynn Smith
(74) *Attorney, Agent, or Firm*—Daniel G. Chapik

(57) ABSTRACT

Oxygen saturation data is monitored during a predefined window to obtain a measurement of circulation delay. The measured circulation delay is used as a basis for determining therapies, including overdrive pacing. In some embodiments, circulation delay is used to identify patients that will benefit from overdrive pacing as a therapy for sleep disordered breathing.

13 Claims, 14 Drawing Sheets

IMPLANTABLE MEDICAL DEVICE WITH CIRCULATION DELAY MEASUREMENT AND THERAPY CONTROL

CROSS-REFERENCE TO RELATED APPLICATION(S)

This application claims the benefit of U.S. Provisional Application No. 60/569,434 filed on May 7, 2004, for "Nocturnal Overdrive Pacing Reduces Circulation Delay" by H. Toby Markowitz, Pooja Mehta, Sameh Sowelam, Chad T. Giese, Mark K. Erickson, Yong K. Cho and Marina Jovanovic.

FIELD OF THE INVENTION

The present invention relates to implantable medical devices and more specifically to implantable medical devices in communication with one or more sensors.

DESCRIPTION OF THE RELATED ART

Sleep disordered breathing (e.g., apnea, hypopnea), periodic breathing, Cheyne-Stokes respiration, and other respiration conditions are of significant and growing medical concern. These conditions, referred to generally herein as disordered breathing, often occur nocturnally during patient sleep (e.g., sleep apnea). In addition, heart failure and other conditions may lead to disordered breathing during waking hours as well.

The prevalence and effects of disordered breathing are becoming better understood. Disordered breathing is often a comorbidity of a whole host of serious conditions such as, for example, heart failure, hypertension, daytime sleepiness, cardiac arrhythmias, obesity, and depression. At present, it is not clearly understood whether these conditions cause disordered breathing, are caused by disordered breathing, or are otherwise connected. Treatment, reduction, or elimination of disordered breathing shows an immediate benefit in certain areas such as a reduction of hypertension, which may also positively affect one or more aspects of a heart failure condition. Of course, for sleep disordered breathing, beneficial therapy leads to better, restful sleep and the benefits thereof. Thus, therapy is not only beneficial for treatment of disordered breathing, but is also beneficial with respect to various comorbidities.

Respiration is generally controlled, directly or indirectly, by the relative quantities of blood gases; notably oxygen and carbon dioxide. The presence and quantity of these gases within the blood stream is referred to as the partial pressure (P) of a given gas within the fluid medium. The human chemical receptors typically respond to the $PCO_2$ levels either directly or based upon derivates or surrogates related to $PCO_2$ levels. Generally, $PO_2$ and $PCO_2$ will be inversely correlated; that is, as $PO_2$ increases, $PCO_2$ decreases. An oximeter typically measures arterial oxygen saturation. As $PO_2$ is used herein, it is meant to include any measure of oxygen within arterial or venous blood as well as within any component thereof (e.g., plasma), dependant upon the selected measurement device.

While the various disordered breathing conditions have their own unique parameters, apnea and its effects will be described as an example. Typically, a patient will have normal respiration for a period of time. At some point, there will be a cessation of breathing (apnea) triggered either by an obstructive blockage (obstructive sleep apnea) or by a neurological failure to initiate respiration (central sleep apnea). As the apnea progresses, the $PO_2$ levels decrease and conversely, the $PCO_2$ levels increase. The magnitude of these variations will depend, to some extent, upon whether the event relates to central sleep apnea, obstructive sleep apnea, or a mixed apnea. At some point, the increase in $PCO_2$ levels trigger a transient arousal and a subsequent resumption of breathing; however, sometimes these levels are now so high that the physiological response includes a burst in sympathetic activity and in some cases a reduction in airway resistance that lead to hyperventilation in order to rapidly lower $PCO_2$ levels. Since the chemoreceptors are located some distance from the lungs, there is a phase delay between the onset of apnea and chemoreceptor detection. Thus, the chemical receptor response is not temporally aligned with the apnea or the hyperventilation cycles. The $PCO_2$ levels fall very low and respiration is slowed or caused to be shallow which, in and of itself may lead to or trigger a subsequent apnea. In effect, the breathing rates generate blood gas levels that are too high or too low before being adequately sensed. As such, these patterns often tend to be cyclic or repetitive. Some patients will have hundreds of events during a single night's sleep.

These breathing variations during sleep interrupt the sleep pattern, thus preventing rest with the resultant consequences. In addition, the breathing variations negatively affect pressures within the pulmonary and cardiac systems, which in turn may result in or affect hypertension or heart failure.

While various therapies exist for treating sleep disordered breathing, they typically either involve highly invasive surgeries with minimal success or the continual use of bulky and cumbersome hardware appliances such as CPAP (continuous positive airway pressure) machines, which are often poorly tolerated resulting in lower compliance rates.

Certain studies have been performed that indicate that cardiac pacing at an elevated rate during sleep reduces the AHI (Apnea/hypopnea Index), which is an objective, quantitative measure of certain disordered breathing conditions for a given patient. Sometimes referred to as nocturnal overdrive pacing, this therapy typically paces at a rate of about 10-15 beats/minute (bpm) above the normal or resting sinus rate. The mechanism for this success is currently the subject of debate and research. What has been shown is that this therapy does not equally benefit all patients and often, has no effect at all on the disordered breathing. Furthermore, there has been no known indicator as to who will or will not respond to the therapy and to what degree. As such, overdrive pacing remains as a potential for future therapy to at least a subset of the disordered breathing population.

DETAILED DESCRIPTION

Figure 1A:
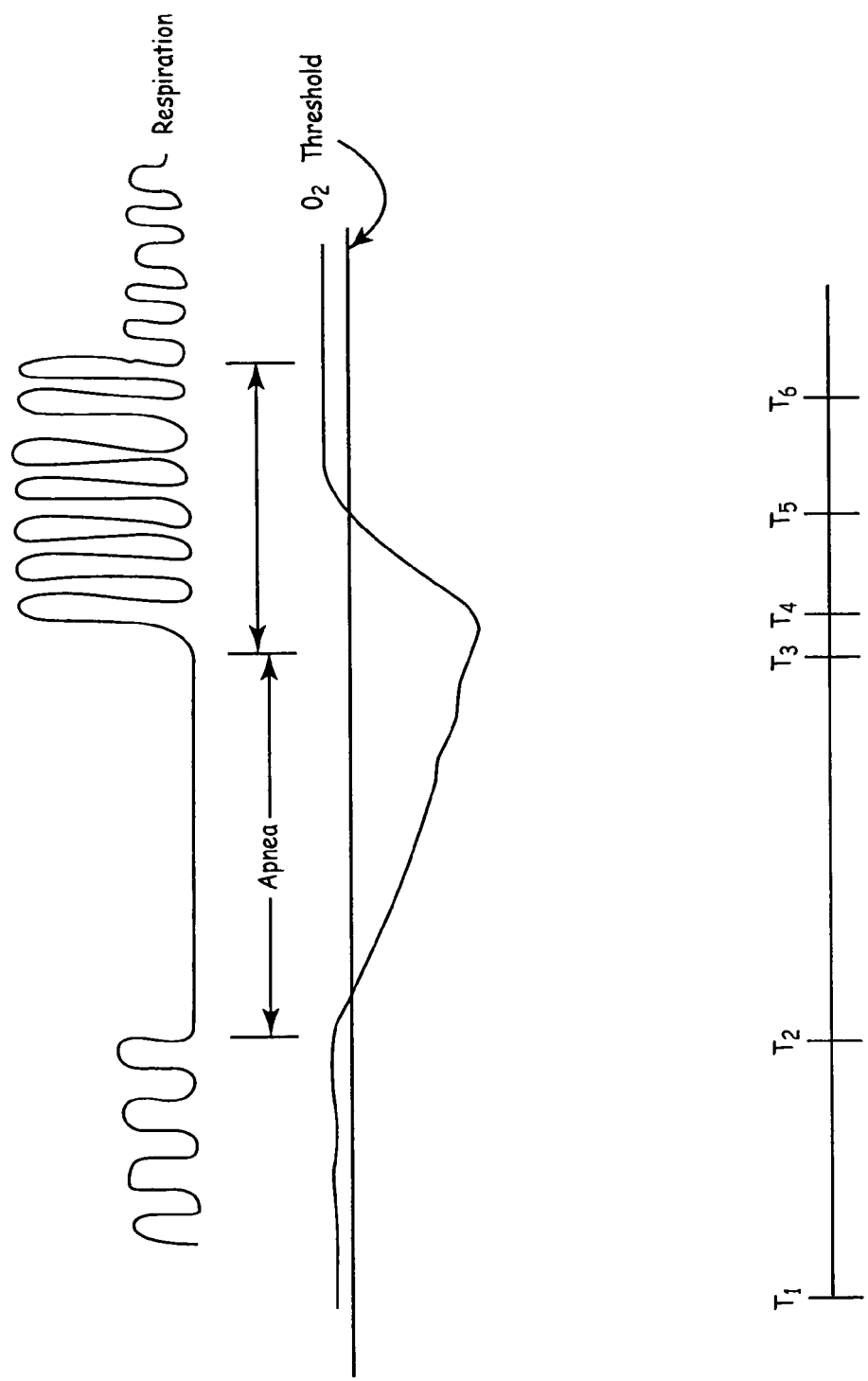
FIG. 1A is a schematic illustration of respiration rates and oxygen saturation prior to, during, and following an exemplary apnea.

FIG. 1A is a graphical representation of respiration and oxygen saturation over time, with oxygen saturation measured within the lungs. From time T1 (and implicitly for some time prior thereto) to time T2, respiration is normal. Oxygen saturation is also normal during this time period. What constitutes, normal arterial oxygen saturation is somewhat subjective and may be denoted as, for example, greater than 90%, 95%, 99%, or any value deemed appropriate. Functionally, this level would be the saturation during normal respiration for a given patient for a given activity level, assuming otherwise normal relevant physiological functioning.

At time T2, an apnea begins. An apnea is the cessation of breathing for some predetermined length of time (e.g., greater than 10 seconds). Thus, from time T2 to T3, there is no respiration. As such, oxygen saturation begins to decrease within the lungs concurrently with the apnea. As explained below, there will typically be a delay between the initiation of the actual apnea and a significant lowering or decline of saturation levels at a remote measurement location, which is not illustrated here for clarity.

Also not illustrated, is an indication of the increasing $PCO_2$ which, by time T3, $PCO_2$ has increased to a point where the appropriate receptor responds and respiration resumes. Alternatively, the patient is aroused from a given sleep state, which causes an increase in autonomic tone and, consequently, tone of the upper airway and terminates an obstructive apnea. More specifically, an obstructive apnea begins in any number of ways, including a central sleep apnea event. The muscles surrounding and defining the airway relax and reduce potency of the airway, preventing inspiration. Expiration may be permitted and negative pressure is developed. Negative pressure in the thorax results from downward movement of the diaphragm. This makes it harder for the heart to expel blood from the ventricles. Continued and often escalating physiological attempts at inspiration through the obstructed airway further increase the negative pressure. Oxygen desaturation accompanies as blood being pumped is not allowed gas exchange with fresh air in the lungs. Desaturation is related to the saturation level at initiation of the event and the duration of the event. Vasoconstriction of the pulmonary vessels increases pulmonary arterial pressure. As attempts to inspire continue, the negative pulmonary pressure reaches a threshold and triggers the brain, which in turn causes arousal. As the patient awakens, muscle tone is increased, the airway opens, and inspiration is permitted. The patient typically does not fully awaken and returns to sleep. Unfortunately, this pattern then repeats itself frequently. Sleep fragmentation and loss of REM sleep have important adverse consequences.

As illustrated in FIG. 1A, the physiological response, upon resumption of respiration, is often to hyperventilate to rapidly expel excessively high levels of $CO_2$ and inspire $O_2$. Hyperventilation continues until time T6, when normal respiration levels resume. That is, the appropriate receptors have determined $PCO_2$ is below the appropriate threshold.

In practice, these transitions would likely be more gradual and may be more difficult to discern than are schematically illustrated. The various sleep disordered breathing conditions dictate the respiration patterns and also relate to the desaturation values. For example, central sleep apnea is neurological in origin and results in a failure to stimulate breathing often resulting in the illustrated hyperventilation when respiration does resume. Conversely, obstructive sleep apnea is a mechanical obstruction (which may be neurologically oriented) of the airway with continued physiological attempts at inspiration. Oxygen desaturation during a given event will be determined by the type of event, event duration, and saturation at initiation of the event.

Even after the resumption of respiration and the onset of hyperventilation at time T3, oxygen saturation begins to increase in the lungs almost immediately, but continues to decline for some period of time at remote measurement locations. The continued decline is due to the finite amount of time required to move a sufficient volume of blood through the lungs; exchange gases; and move the oxygenated blood to the remote measurement point. This is referred to herein as transport delay and is explained further below. The timeframe is relative and dependant upon the measurement point and blood flow. For example, oxygen saturation is commonly measured externally at a fingertip or earlobe with an oximeter, utilizing optical parameters to evaluate oxygen saturation within the fluid medium. Thus, transport delay would be related to the arterial distance between the heart and the fingertip or earlobe as well as blood flow.

Figure 1B:
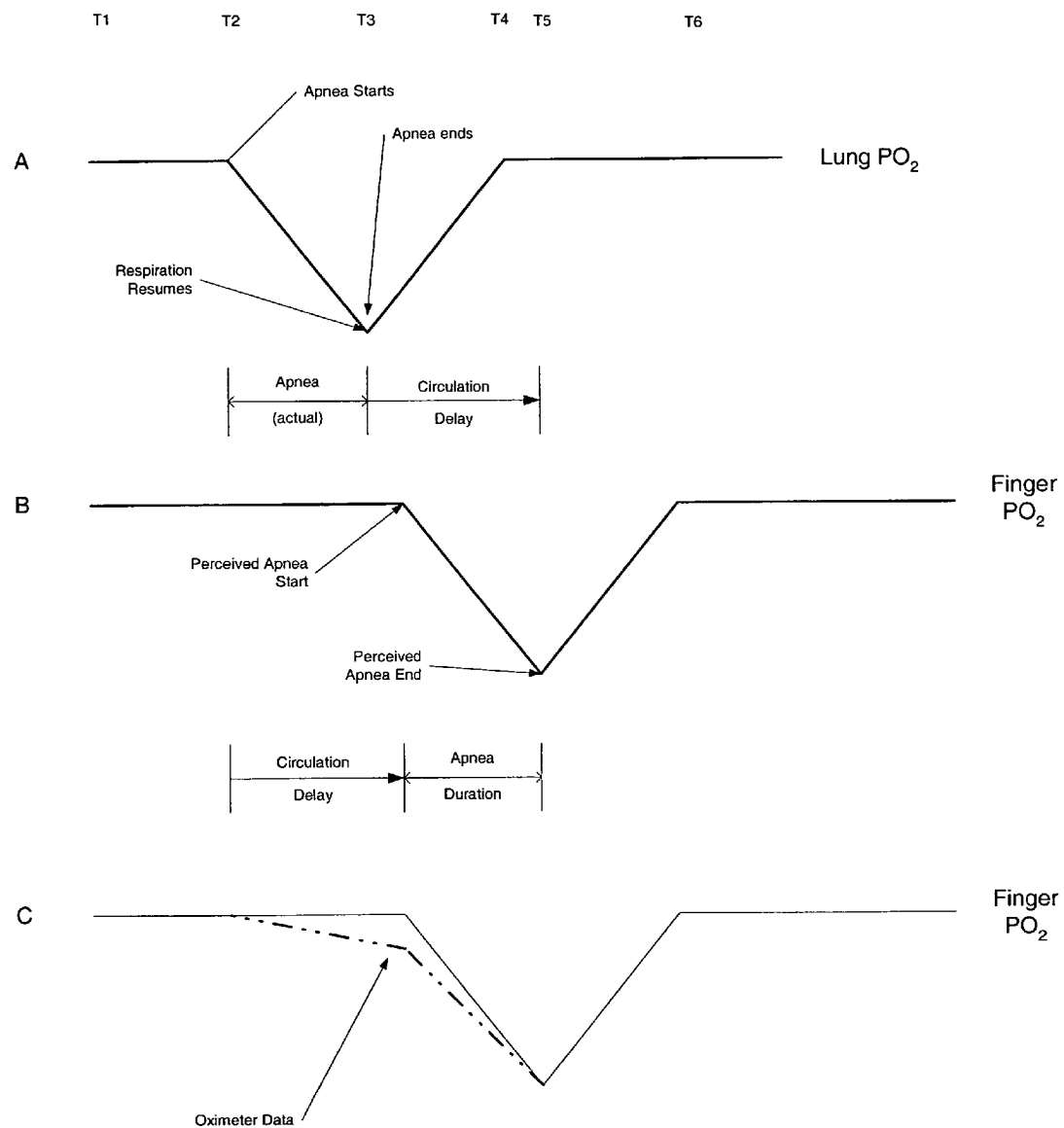
FIG. 1B is a schematic diagram illustrating transport delay.

FIG. 1B schematically illustrates the effect of transport delay in an idealized analysis of circulation delay. Oxygen saturation levels shown in panels A, B, and C are each temporally aligned. The saturation level illustrated in panel A represents $PO_2$ within the lung. In panel B, $PO_2$ is illustrated as measured in a finger, which is a common measurement point but is also simply indicative of an anatomical location that is remote from the lungs and heart.

Referring to the lung level (A), $PO_2$ is initially normal. Almost immediately after the initiation of an apnea, $PO_2$ begins to steadily decline until the apnea ends and respiration resumes. Again, $PO_2$ begins to almost immediately increase in the lungs as soon as respiration commences. The illustrated apnea initiation and termination are indicated as the "Apnea (actual)."

Referring to the finger oxygen saturation level in panel B, there is a delay between the initiation of the apnea and the perceived decrease in $O_2$ saturation. The perceived start of the apnea is meant to indicate where measurements made at the finger (or other remote location) illustrate the initial decline in $O_2$ saturation due to the apnea. This is simply due to the finite amount of time or transport delay required for any given bolus of blood to flow from the heart to the remote measurement point. Thus, as the apnea starts and the lungs are deprived of oxygen, previously oxygenated blood continues to flow throughout the circulatory system. Eventually, the blood that arrives at the remote location will be $O_2$ depleted and the effects of the apnea are apparent at the remote location. The effect of transport delay was not apparent in the previously described example of FIG. 1A since that illustration described action within the lungs, not at a remote measurement location.

The finger saturation level in panel B is stylized and idealized as illustrated. Thus, the apnea duration (as monitored by the finger sensor) exactly corresponds to the actual apnea in terms of time duration. The shift between the start of the actual apnea and the perceived start of the apnea corresponds to the circulation delay. Thus, the shift from the termination of the actual apnea to the perceived termination also corresponds to the circulation delay. In practice, there may be variations between the actual and perceived apnea lengths. These variations may be physiological and/or sensor anomalies. As addressed below, these variations, if present, may be used to evaluate the quality and usability of a given data set.

Referring to both FIGS. 1A and 1B, the events are identified by common timing indicators T1-T6. Oxygen saturation continues to decline due to transport delay until time T5, at which point the saturation level begins to increase until it normalizes at time T6. Circulation delay (CD) is the time from the resumption of respiration (T3) until oxygen saturation begins to increase from its lowest (remote) point or nadir (T5). Circulation delay is an indication of transport (flow); namely, how quickly oxygenated blood flows through the body. Circulation delay may be measured from the actual onset to the perceived onset as well as from the actual termination to the perceived termination.

Finger saturation level (C) illustrates the idealized saturation levels (i.e., "B") in solid lines as compared to exemplary saturation levels in dashed lines, approximating those that might actually be sensed. As illustrated, there is often an almost immediate but less significant decline in oxygen saturation measured at a remote location (e.g., finger) that begins approximately with the initiation of the actual apnea. Though previously oxygenated blood continues to flow after the initiation of the event, the volume of the blood and its available oxygen are limited. Cells along the arterial path continue to absorb oxygen, which rapidly begins to deplete this now finite simply. Thus, even remote measurement locations will have a rapid and often detectable decline in oxygen saturation.

This lesser desaturation continues until the "perceived initiation" of the event. When the "perceived initiation" of the event occurs, then the decline measured at the remote location is more consistent with the degree of change illustrated in the lung saturation levels. The actual point of transition, while illustrated clearly, may not be so readily apparent in actual sensor data.

Thus, in practice it becomes more difficult to identify the perceived apnea initiation from the remote sensor data. As such, measuring circulation delay from the termination of the apnea to the perceived termination of the apnea often is less complex and provides for more accurate results.

In one embodiment of the present invention, overdrive pacing is delivered to a patient nocturnally, during periods of sleep, or during waking hours at an elevated rate with respect to either an intrinsic or sensor indicated sinus rate. The elevated rate may be anywhere from 1 to 30 bpm above the sensor rate and potentially even higher. In certain embodiments, the elevated rate is approximately 10-15 bpm above the resting rate.

Referring again to FIGS. 1A and 1B, the circulation delay measured during overdrive pacing is significantly shorter or reduced in comparison to the circulation delay CD without pacing. For example, circulation delay may be from time T3 to time T4, rather than to time T5. The higher heart rate increases cardiac output (i.e., stroke volume times heart rate) and more quickly delivers oxygenated blood through the arterial system to the measurement point. Furthermore, though not separately illustrated, this effect will tend to permit the receptors to more quickly identify the reduction in $PCO_2$, thus leading to a shortened period of hyperventilation in some cases. Similarly, the same receptors will sense the elevated $PCO_2$ levels more quickly after the onset of the apnea (T2), and again, in some cases reduce the length. Pacing may have an immediate impact on circulation delay. Alternatively, pacing over time may be required to observe a reduction in circulation delay trends.

The overdrive pacing rate can be determined or optimized to provide the appropriate reduction in circulation delay. Embodiments of the present invention are utilized to reduce circulation delay, which in and of itself produces various therapeutic benefits. For example, in patients having sleep disordered breathing, reduction of the circulation delay may result in less daytime sleepiness even for those patients where overdrive pacing does not significantly lower the AHI. That is, even if the number of events is not decreased by the therapy, reducing the circulation delay may reduce the effect of these events. Furthermore, reduction in circulation delay may lead to a reduction in atrial arrhythmias, reduce hypertension, reduce hypoxia, reduce dependence upon medications, and positively affect catacolamine levels. Using pacing as a means to reduce circulation delay also prevents bradycardia, which otherwise might occur during apnea. Significantly, the reduction of the circulation delay improves endothelial dysfunction. That is, lower oxygen saturation levels lead to damage of these cells on the interior vessel walls. Reducing circulation delay lowers the exposure of these cells to desaturated blood. The other benefits result from a more even delivery of oxygen; reduction of pressure variations; more even respiration patterns and the like.

As mentioned, not all sleep disordered breathing patients respond to nocturnal overdrive pacing as a means to reduce or eliminate apneas or hypopneas, typically evidenced by a reduction in the AHI. Conversely, the present invention reduces circulation delay in a much larger percentage of patients.

One embodiment of the present invention utilizes a measure of circulation delay to formulate a predictive indicator to identify which sleep disordered breathing patients are likely to respond favorably to pacing in order to reduce their AHI. This is accomplished by measuring the reduction in circulation delay, either as a percentage or in terms of magnitude. Patients whose reduction exceeds a predetermined value are indicated to likely have a reduction in AHI by using pacing as a therapy for sleep disordered breathing. Alternatively, patients whose normal circulation delay exceeds predetermined guidelines may likewise be indicated as potential candidates. It should be appreciated that circulation delay is affected by the measurement location. In addition, relative changes from a patient established baseline may be used or the patient values may be compared to statistical norms and evaluated based on sensed absolute values. Patient baselines may be established by monitoring circulation delay during periods of sleep. In addition, patients can hold their breath to establish a waking baseline. This data may further highlight the effect of events (e.g., apnea) during periods of sleep versus waking periods. Comparing the nocturnal baseline to the waking baseline may be used as a predictor of likely therapy, success.

Figure 2:
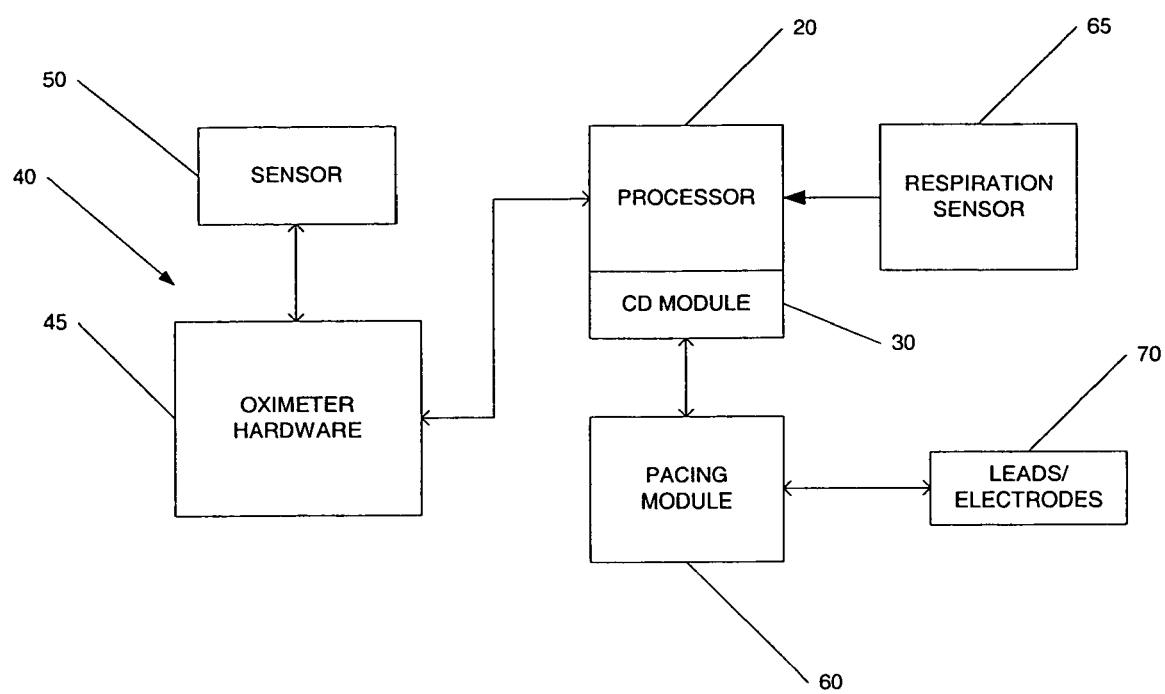
FIG. 2 is a schematic diagram of a system for monitoring oxygen saturation and providing pacing therapy.

FIG. 2 is a schematic illustration of one embodiment of the present invention. A system 10 includes a processor 20. Included therewith are any appropriate electronic components, hardware, software, memory, and the like. A circulation delay module 30 is communicatively coupled with the processor 20 or forms a portion of the processor 20. An oximeter 40 includes any required hardware/electronics 45 as well as a sensor 50. The oximeter 40 is communicatively coupled with the processor 20. The oximeter 40 may be any device that measures the relative oxygen saturation within an arterial bloodstream. Examples include optical arrangements that emit and measure electromagnetic energy passed through or reflected from a blood supply, chemical sensors (direct or proxy), biological sensors, or the like. The hardware/electronics 45 and sensor 50 may be separate components or integrally housed.

In addition, various embodiments of the present invention utilize respiratory data. An appropriate respiration sensor 65 is communicatively coupled with the processor. Respiration sensor 65 may be a minute ventilation sensor, motion sensor, temperature sensor, or any appropriate sensor or combination of sensors that indicates respiration. Respiration data is passed via an appropriate communication medium to the processor 20.

In certain embodiments, a pacing module 60 is provided and includes appropriate leads and electrodes 70 that sense cardiac events and deliver electrical stimulation from the pacing module 60 to cardiac tissue. It should be appreciated that all of the components illustrated may be implanted within a patient, provided external to the patient, or any combination thereof. Furthermore, all or any subset of these components may be integrally housed or provided as separate components.

With such a system, oxygen saturation data as well as circulation delay measurements can be used within the device or by a caregiver as discussed herein. In addition, these data may be communicated from the implantable device to a centralized database, such as for example, Medtronic's CareLink Network™. This data may be analyzed remotely, trends may be monitored, therapies and setting may be determined, and instructions or parameters may be provided to the implanted device.

When overdrive pacing is utilized, the non-paced circulation delay may be periodically obtained to determine the effects of the therapy. That is, pacing may be withheld for a period of time. The amount of time may vary depending upon how long it takes for apnea and/or baseline circulation delay to return.

Figure 3:
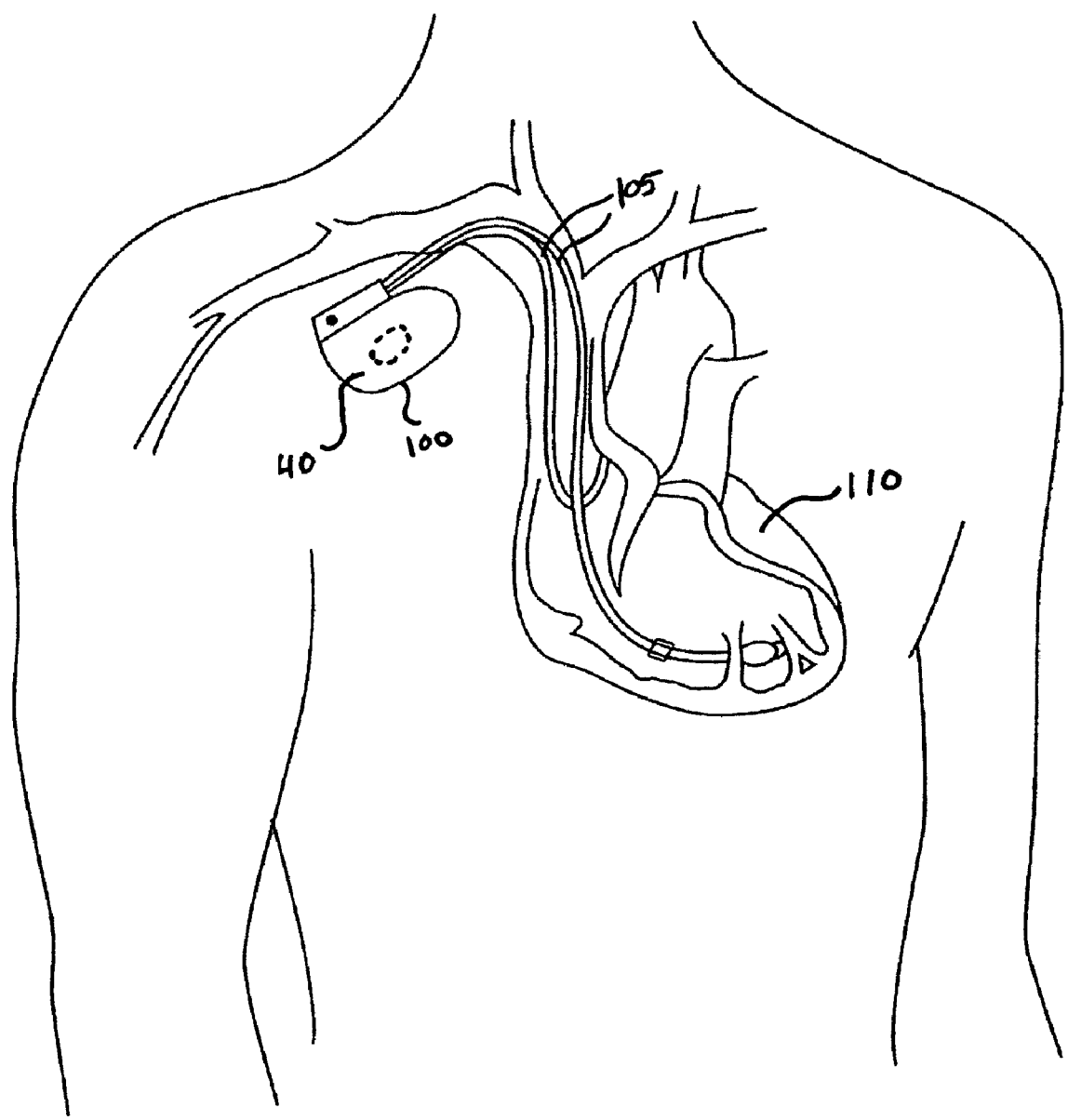
FIG. 3 is an illustration of an implantable medical device having an oximeter.

FIG. 3 illustrates an implantable medical device IMD 100 that includes pacing module 60. One or more leads 105 are placed within the patient's heart 110 at suitable sites. To provide overdrive pacing, the IMD 100 will generally include a lead 105 disposed within the atrium to control cardiac rate. One or more leads 105 may be disposed within the right and/or left ventricle for ventricular pacing and the IMD 100 may include defibrillation or other capabilities.

The oximeter 40 is integral with the housing of the IMD 100. The oximeter 40 includes a light emitter and a light collector for measuring the relative amount of light absorbed by oxygenated hemoglobin, thus indicating the degree of oxygen saturation. Typically, light is emitted at two or more wavelengths. The collector is positioned to receive reflected light and the IMD 100 is positioned during implantation such that the oximeter is proximate arterial blood flow. Generally, the oximeter 40 would be positioned facing "downward" (as illustrated) or towards the interior of the patient. The oximeter 40 could be positioned on the upper surface (as implanted) of the IMD 100 if proximity to arterial blood flow is achieved. The output of the oximeter 40 is provided to the processor 20 of the IMD 100 and is used to measure the patient's circulation delay with the CD module 30.

With the oximeter 40 formed as an integral part of the IMD 100, implantation is generally not hindered or complicated. In an alternative embodiment, one component of the oximeter (e.g., the collector or the emitter) may be separated and individually positioned so as to permit analysis of light or other electromagnetic energy that passes through an arterial supply, rather than light that is reflected. The separate component may be coupled to the IMD 100 via one or more wires or may communicate via telemetry.

Figure 4:
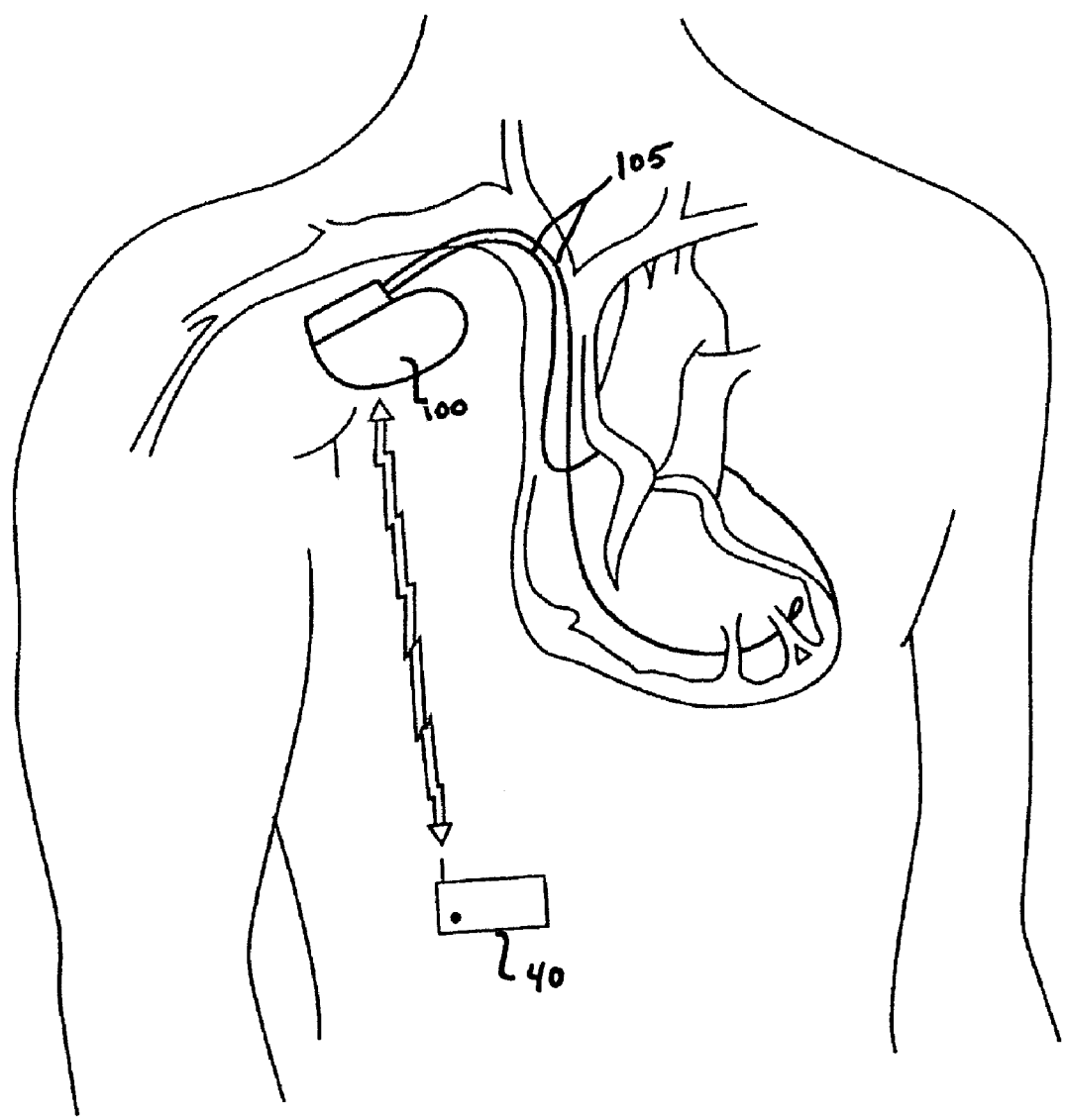
FIG. 4 is an illustration of an implantable medical device in communication with an implanted oximeter.

FIG. 4 illustrates an embodiment wherein the oximeter 40 is implanted remotely from the IMD 100. The oximeter 115 communicates with the IMD 100 via telemetry and provides oxygen saturation data for use by the CD module 30. Alternatively, the IMD 100 and the oximeter 40 could communicate to a separate, external device (not shown) that either acts to exchange information between the two components or processes the data and determines circulation delay. Of course, the specific implantation site of the oximeter 40 will define the normal circulation timing and parameters, such as transport delay. Thus, with greater distance from the lungs, the delay between cardiac or pulmonary events (e.g., the resumption of breathing) and a sensed change in oxygen saturation will correspondingly and normally be longer. While not limiting, the implantation site of the oximeter 40 should be considered when establishing timing parameters.

Figure 5:
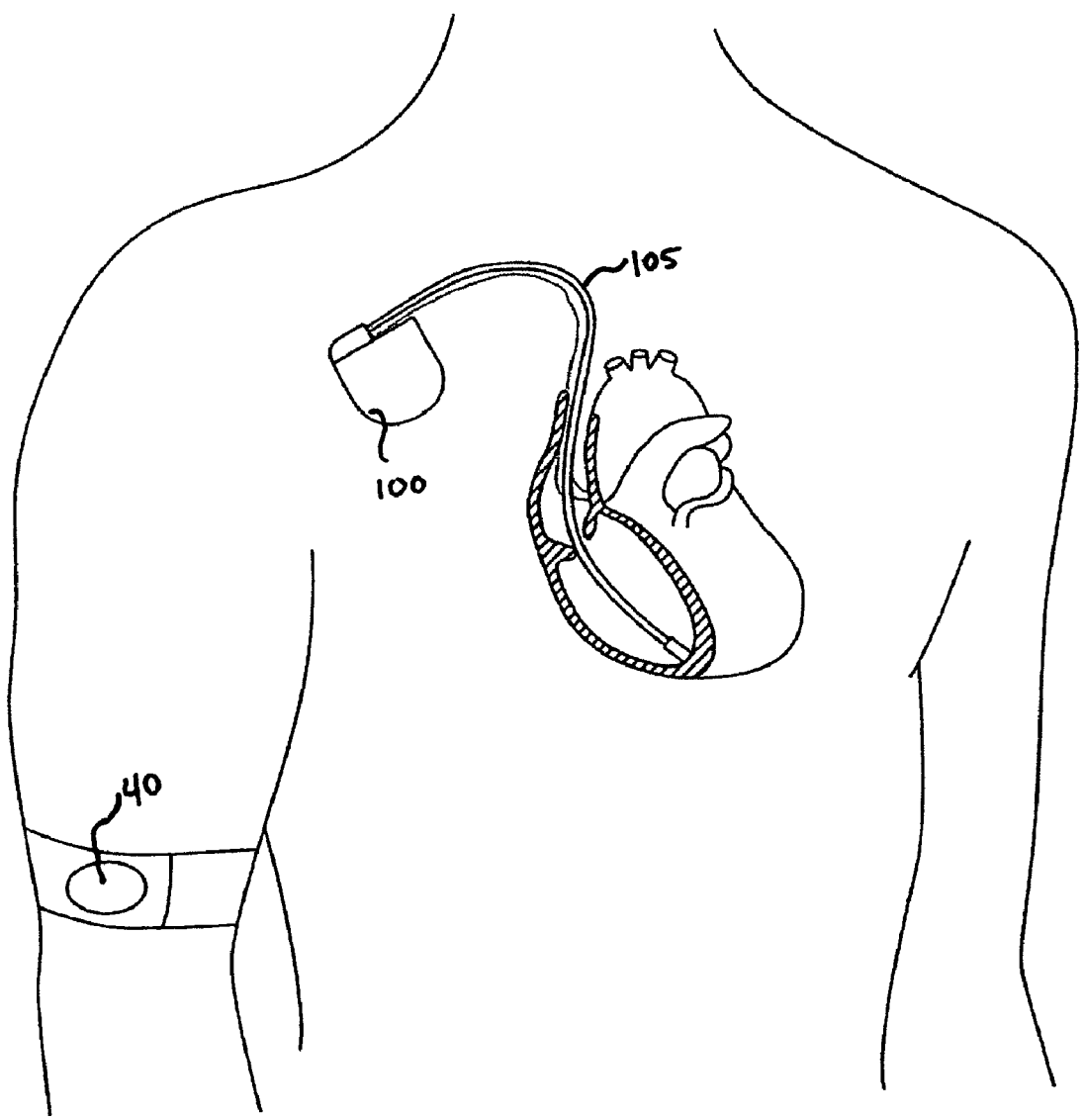
FIG. 5 is an illustration of an implantable medical device in communication with an external oximeter.

FIG. 5 illustrates an embodiment wherein the oximeter 40 is externally coupled with the patient. The external oximeter 40 communicates via telemetry with the IMD 100 to provide data to calculate the circulation delay. Alternatively, this data is provided to an external processor and the circulation delay is calculated therein. The external oximeter 40 is positioned in any location that provides sufficiently accurate oxygen saturation measurements. The position of the oximeter 40 and the method of attachment are selected depending upon the patient's condition and the desired therapy. For example, for nocturnal pacing the oximeter 40 should be securely but comfortably attached.

Figure 6:
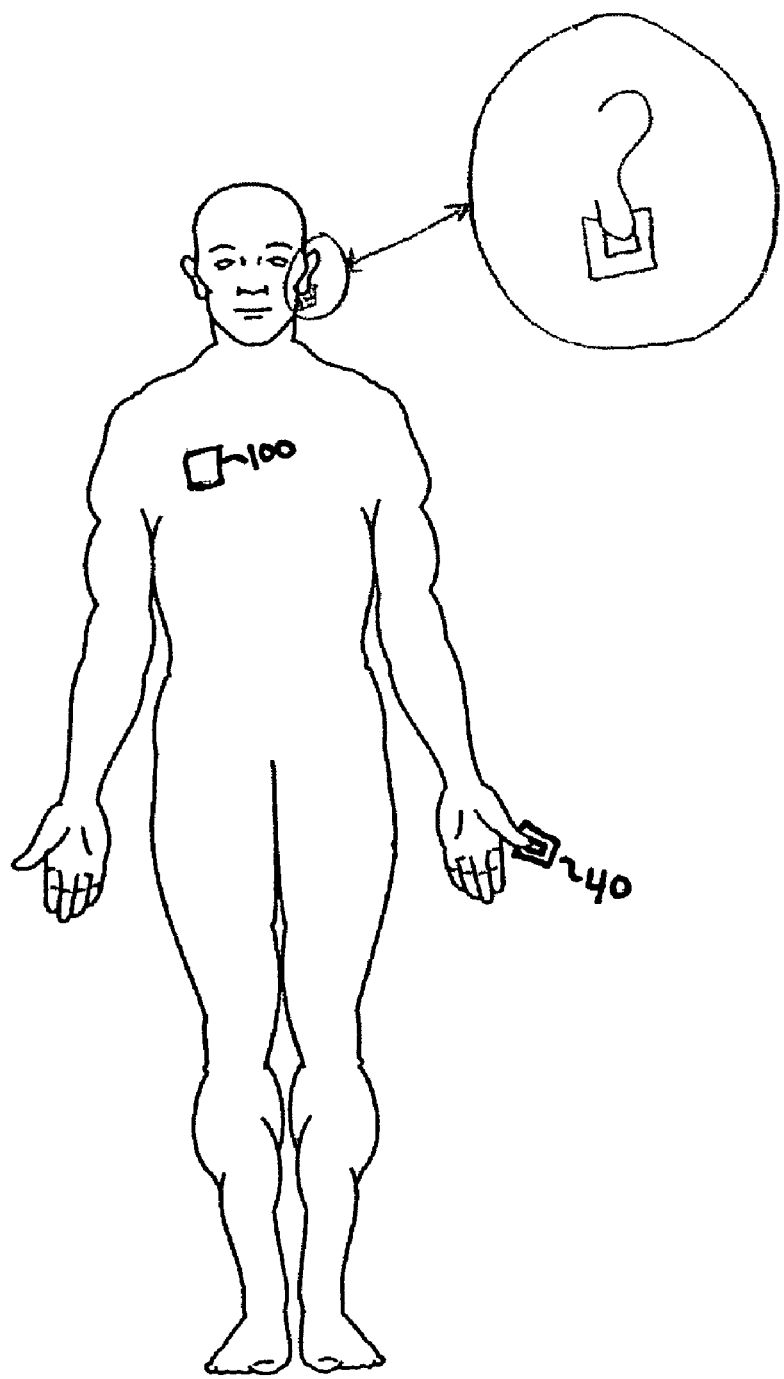
FIG. 6 is an illustration of an implantable medical device in communication with an external oximeter.

FIG. 6 illustrates alternative, exemplary external positions for the oximeter 40. The oximeter 40 is "clipped" to a fingertip or earlobe. These locations permit sufficient light transmission and are typically conveniently accessible. Once again, IMD 100 is illustrated and is communicatively coupled with the oximeter 40, either directly or via a separate external device (not illustrated). Alternatively, where baseline circulation delay measurements are desired, the patient might not yet have an IMD 100 or one that is in communication with the oximeter 40. Thus, the circulation delay measurements may be made to determine which patients would respond to pacing therapies for disordered breathing.

Figure 7:
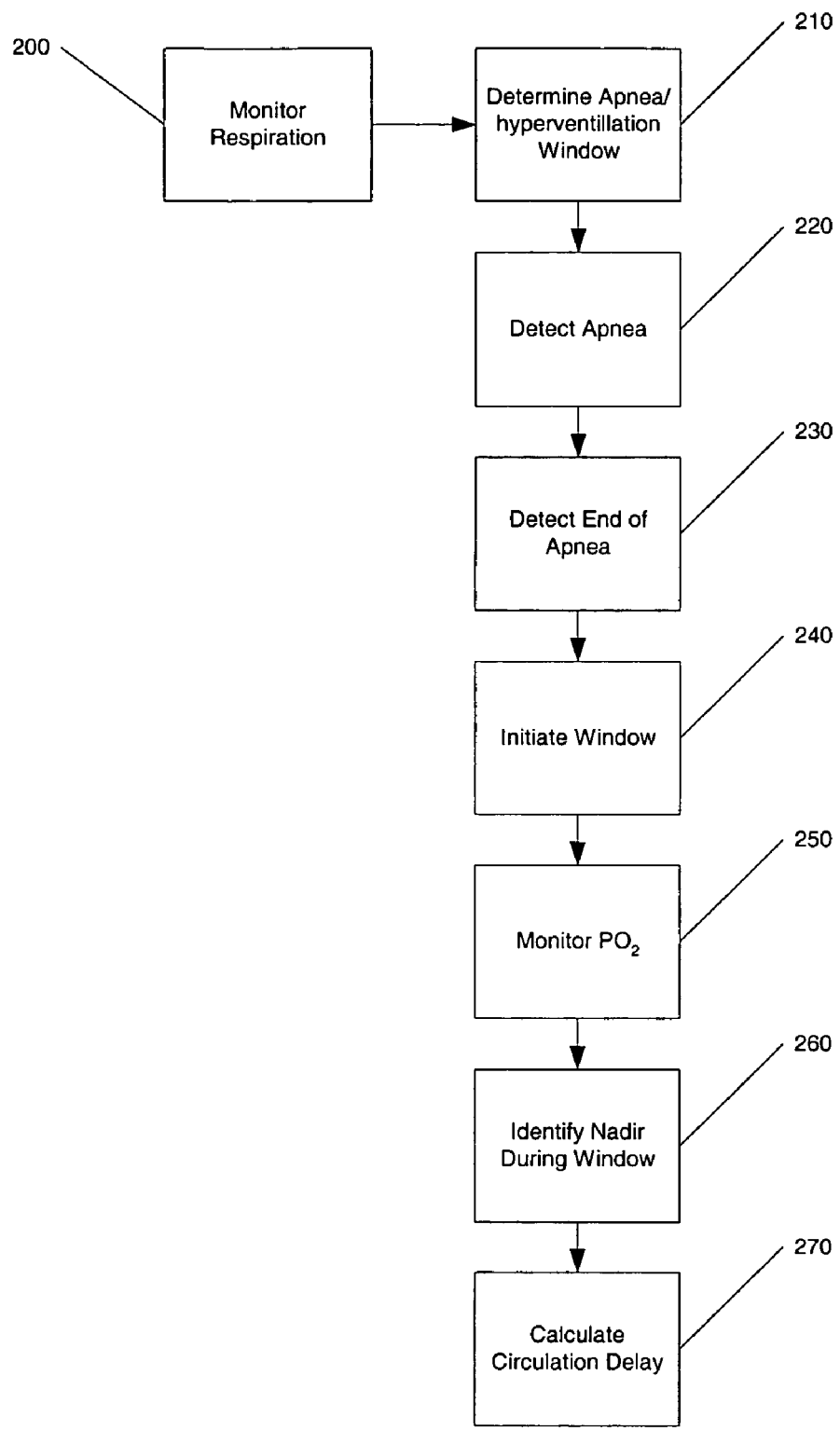
FIG. 7 is a flowchart illustrating a process of calculating circulation delay.

FIG. 7 is a flowchart illustrating a process for measuring circulation delay. The patient's respiration is monitored (200) using an appropriate sensor. For example, impedance based minute ventilation sensors, motion sensors, nasal temperature sensors, or the like may be utilized. Thus, the respiration sensor may be external to the patient, implanted, or implanted and included within an IMD. In addition, in certain cases circulation delay will be measured in a clinical environment, for example, during a sleep study or office visit. In such a case, the various respiration sensors are available. In addition, circulation delay may be measured during a waking state. For example, having the patient hold their breath causes a controlled "apnea". While the above sensors are again available, in such a case it would also be possible to manually observe and indicate the cessation and resumption of breathing.

As illustrated in FIGS. 1A and 1B, typical relevant respiration patterns include apnea or hypopnea, often followed by a period of hyperventilation. In the illustrated example, the apnea begins at time T2 and hyperventilation ceases (i.e., normal respiration resumes or another apnea/hypopnea begins) at time T6. As previously indicated, the initiation of hyperventilation and the cessation of the apnea generally coincide (e.g., time T3). Thus, the period of hyperventilation following an apnea is referred to as the "apnea/hyperventilation" window. This window defines the period of time during which the nadir of oxygen saturation is identified. Alternatively, circulation delay could be based upon achieving normal oxygen saturation and as such the window would be defined accordingly. Furthermore, the present embodiments are described with respect to apneas. Other events (e.g., hypopnea) could also be used to define the window, depending upon the condition in question.

The window is determined (210) by monitoring the duration of at least one relevant episode, such as for example, an apnea and subsequent hyperventilation. Several such episodes may be monitored and averaged. Finally, updating the duration data may continually or periodically modify the window over time. The particular breathing disorder will determine the relevant events to monitor in determining the window.

Once the window has been determined (210), the system monitors for a relevant triggering event, such as an apnea (220). The end of the apnea is identified (230) and triggers the initiation (240) of the window. During the window, oxygen saturation values are evaluated (250) and the lowest, non-anomalous point occurring during the window is designated as the nadir (260). Anomalous data is ignored. For example, sensor dislodgement or physical/optical/electrical interruption may produce values at or about zero and noise or other factors may produce similar spurious results.

Once the nadir is identified, circulation delay is obtained by calculating (270) the time interval from the initiation of the window to the nadir. Once so obtained, the circulation delay data is provided to the appropriate device and output or utilized accordingly. These measurements may be made and utilized in real-time, on a delayed basis (e.g., upon expiration of a window, etc.), or the data may be collected over a period of time and analyzed at a later time. This represents circulation delay for a single event and may be used accordingly. Alternatively, data from many events may be collected. From this collection, circulation delay may be obtained relevant to any elongated period of time, rather than on an episodic basis. Thus, as circulation delay is used herein, the term may refer to an episodic determination or to a value based on a collected data set over time.

Figure 8:
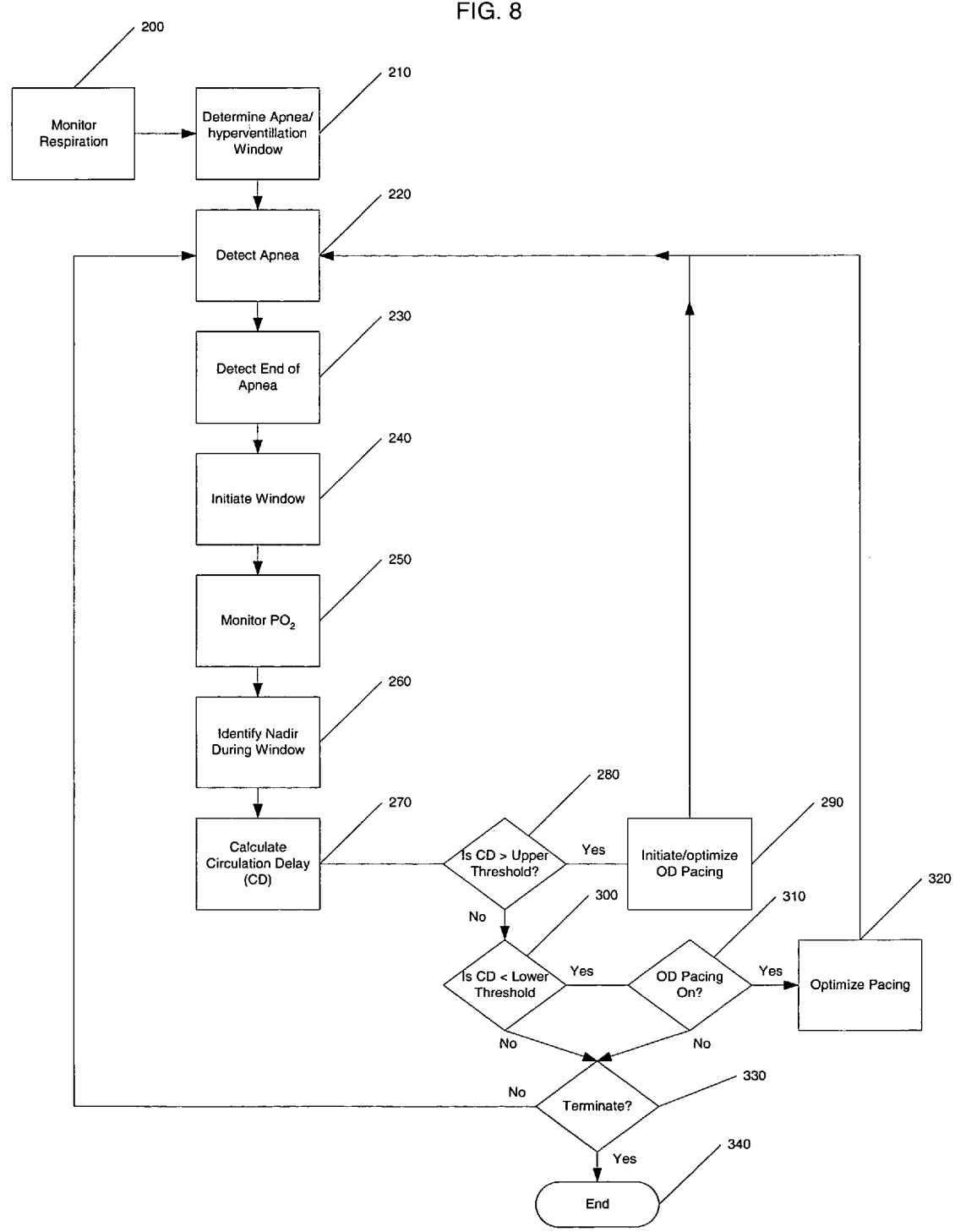
FIG. 8 is a flowchart illustrating a process of utilizing a calculated circulation delay in managing a pacing regime.

FIG. 8 is a flowchart illustrating a process wherein a patient has an IMD that includes pacing capability. By utilizing predetermined threshold values, overdrive pacing is selectively initiated, modified, or terminated to modify circulation delay. The process may be automated, e.g., within an IMD, or performed manually. Steps 200 through 270 are similar to those of FIG. 7. The circulation delay (CD) that is calculated (270) is then further analyzed. If the measured CD exceeds a predetermined upper threshold (280), then overdrive pacing is initiated (290). Overdrive pacing will reduce or shorten the circulation delay and address the various comorbidities discussed above. Alternatively, if the CD exceeds the threshold and overdrive pacing has already been initiated, then the overdrive pacing is optimized (290) by increasing or decreasing the rate until the desired effects are achieved.

If the measured CD is below the upper threshold (280), the value is compared to a lower threshold value (300). If the CD is below the lower threshold value and overdrive pacing is occurring (360), the pacing regime is optimized (320). The lower threshold represents an acceptable value and if the CD is below this value, then the pacing rate might be lowered while still achieving acceptable results. As should be apparent, circulation delay will not be mechanically lowered to an undesirable rate; thus, the lower threshold is a basis for optimizing pacing and conserving battery life. As such, the lower threshold comparison is optional.

If the CD is below the lower threshold or overdrive pacing is not engaged (310) then a decision to terminate (330) the process is made. The process is terminated if this was an initial evaluation of circulation delay and the parameters are normal. The process is continued (330) if overdrive pacing is utilized or if continual or periodic monitoring of circulation delay is desired.

Figure 9:
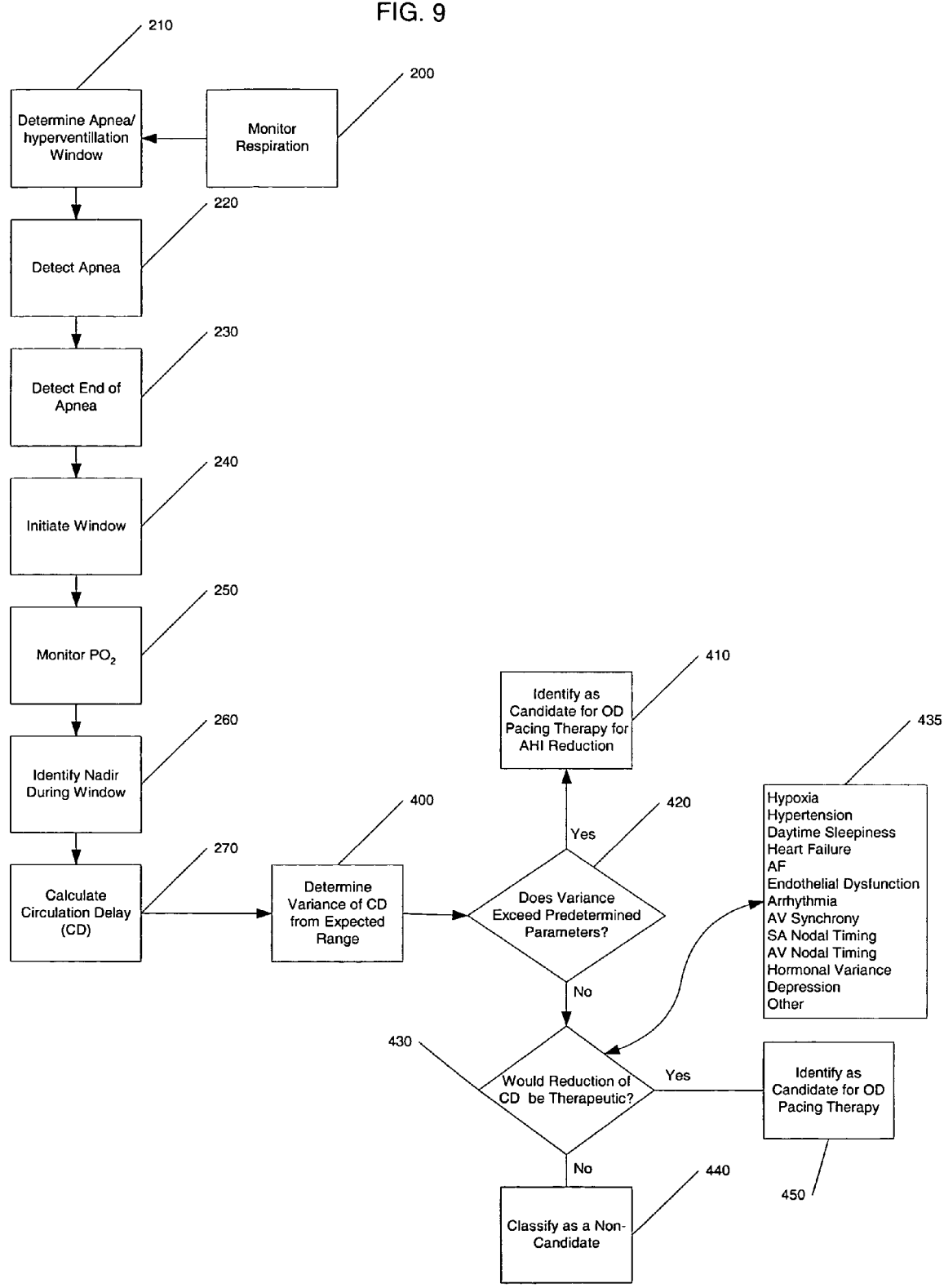
FIG. 9 is a flowchart illustrating a process of utilizing measured circulation delay to identify patients that would benefit from a pacing therapy.

FIG. 9 is a flowchart illustrating a process of utilizing measured circulation delay to gauge the therapeutic benefits of overdrive pacing. Steps 200 through 270 are similar to those discussed with reference to FIG. 7. Once obtained, the measured circulation delay is compared (400) with an expected normalized value or range. This expected value may be obtained from generalized medical and demographic data, e.g., age, sex, physical condition, medical status, etc. In addition, patient specific variables could be considered in determining what the expected circulation delay for a given patient should be. In addition, the patient's current medical status may affect the threshold values that are chosen. For example, a patient having heart failure would not be expected to have the same values as an otherwise healthy patient. Likewise, what may be of modest benefit (e.g., in terms of circulation delay values or improvements) to the otherwise healthy patient may be of enormous benefit to a heart failure patient. Thus, the selected threshold values are chosen accordingly.

The measured circulation delay is compared to this expected value and a variance is obtained. If the variance exceeds predetermined parameters (420), then the patient is identified (410) as a candidate for overdrive pacing as a therapy for sleep disordered breathing with the objective goal of lowering the patient's AHI. That is, if the measured circulation delay exceeds the expected value by more than this predetermined amount, then the resultant decrease in circulation delay achievable through overdrive pacing along with its other effects will likely decrease the AHI. The values may be expressed in terms of magnitudes or percentage variances. The values for these parameters are established based upon patient demographics. Alternatively, if possible, overdrive pacing may be provided in a test setting where the actual reduction in circulation delay and/or the new circulation delay value itself may be analyzed to determine the effectiveness of overdrive pacing as a therapy for sleep disordered breathing.

If the measured circulation delay exceeds the expected range (400), but the variance does not exceed the predetermined parameters, then a determination (430) is made as to whether overdrive pacing to reduce circulation delay may be therapeutic for reasons other than lowering the AHI. Of course, it should also be appreciated that for patients who do not have sleep disordered breathing, the following considerations would also apply, whether or not the variance exceeds the predetermine parameters (420).

Assuming the patient's measured circulation delay is within the expected range, then reduction through pacing would not likely be therapeutic absent some other intervening factor. As such, the patient is classified (440) as a non-candidate for overdrive pacing for purposes of the present invention.

Alternatively, if the circulation delay is prolonged and, thus, may be beneficially reduced through pacing, the patient's medical condition is considered to determine whether such a reduction would be therapeutic. As previously stated, reducing of circulation delay through pacing often results, directly or indirectly, in less hypoxia, a decrease in hypertension, reduction in daytime sleepiness, reduction in AF, reduction in other arrhythmias, decreased endothelial dysfunction, improved AV synchrony, improved SA nodal timing, improved regulation of AV delay, hormonal stabilization, improved mood (e.g., depression), as well as others. If the patient has one or more of these issues and an therapeutic reduction in CD is achievable, the patient is classified (450) as a candidate for pacing therapy.

In practice the decision (430) may be a subjective medical decision to determine whether the reduction in circulation delay and the improvements achieved would warrant implantation of the IMD 100. If the patient already has the IMD 100 or has been indicated to receive one, the decision is simply whether to enable overdrive pacing as a therapy. Again, the decision would be based on the potential therapeutic benefits in contrast to the increased power consumption.

Alternatively, this decision making process may be automated within the IMD 100 and/or external device in communication with the IMD 100. That is, the measurement and analysis of circulation delay occurs and the data is provided to the IMD 100. Based upon the variance, the IMD 100 selective enables the overdrive pacing as a therapy. In order for the IMD 100 to determine (430) if pacing would be therapeutic with variances below the predetermined parameters, additional patient data is required. Such data may be provided by implanted or external sensors in communication with the IMD 100, such as blood pressure monitors. Alternatively, coded patient medical information may be provided to the IMD 100 from an electronic medical record, or similar source.

Figure 10:
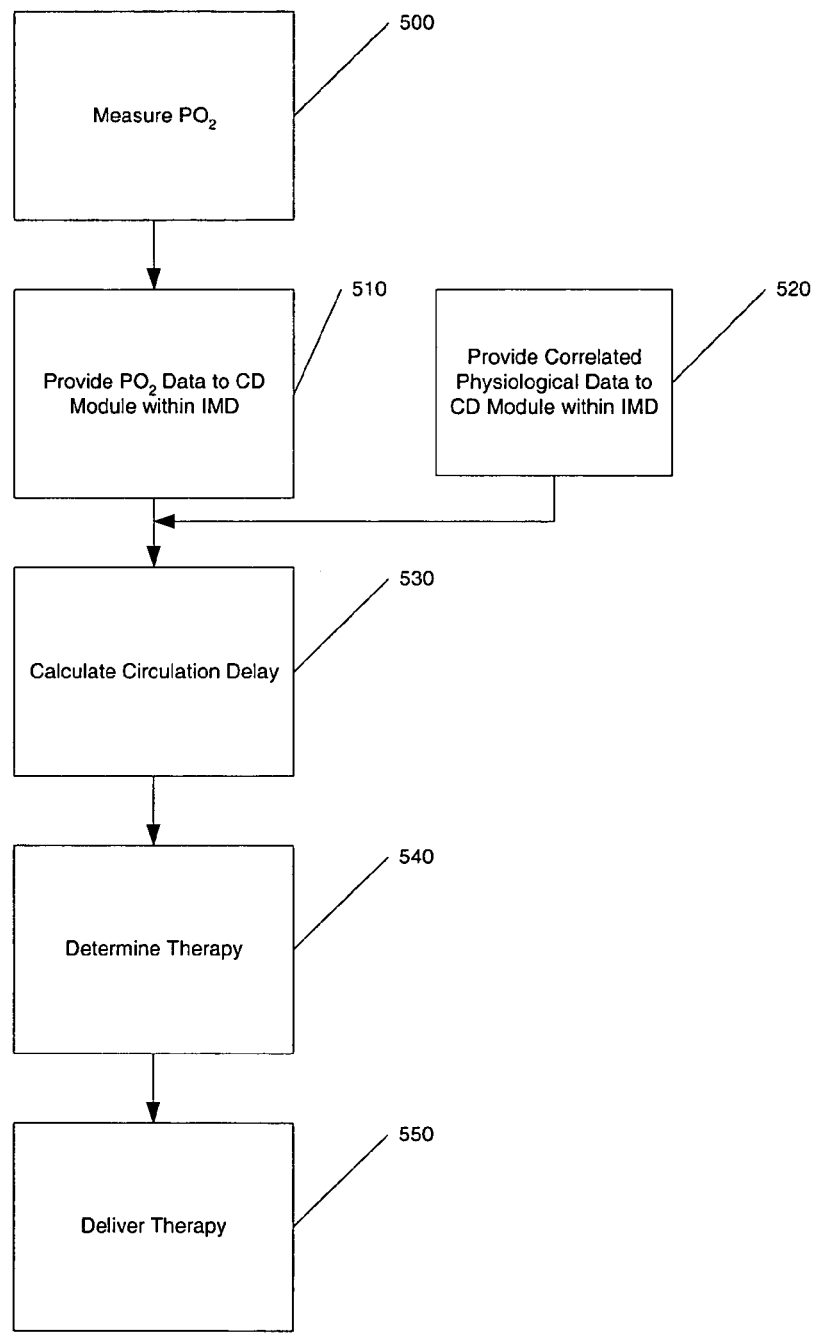
FIG. 10 is a flowchart illustrating a process wherein an implantable medical device determines therapy settings based upon measured circulation delay.

One embodiment of such an automated process is illustrated in the flowchart of FIG. 10. Oxygen saturation is measured (500) and provided (510) to the circulation delay module of IMD 100. Correlated physical parameters are also provided (520). The physical parameters would include respiration rate, respiration timing, apneas, hypopnea, and the like. The IMD 100 calculates (530) the circulation delay and based upon the previously described processes, determines (540) what, if any, therapy, is appropriate to reduce the circulation delay. If therapy is warranted, the IMD 100 implements (550) that therapy. Though not illustrated, the IMD 100 may communicate with an external device or otherwise provide information to the patient or medical personnel. Such communication informs the patient and medical personnel of the selected therapies or advises of conditions wherein the IMD 100 is unable to evaluate the parameters.

As previously discussed with respect to FIGS. 1A and 1B, circulation delay is measured based upon various physiological responses. In general, circulation delay may be thought of as the amount of time required by the cardiovascular system to effect a change at a given location after an initiating event. Thus, in FIGS. 1A and 1B, the initiating event is the resumption of respiration/hyperventilation at time T3. The change effected is the point at which oxygen saturation begins to increase. Thus, the termination of the apnea is noted along with the nadir of oxygen saturation. Alternatively, the change effected could be the point at which oxygen saturation crosses the threshold or any other predefined value. While the present embodiments are described in the context of an apnea followed by hyperventilation, they are not so limited and it should be appreciated that the particular disordered breathing condition will define the initiating event and the change effected, as well as any events used to denote, predict, or identify the same.

Figure 11A:
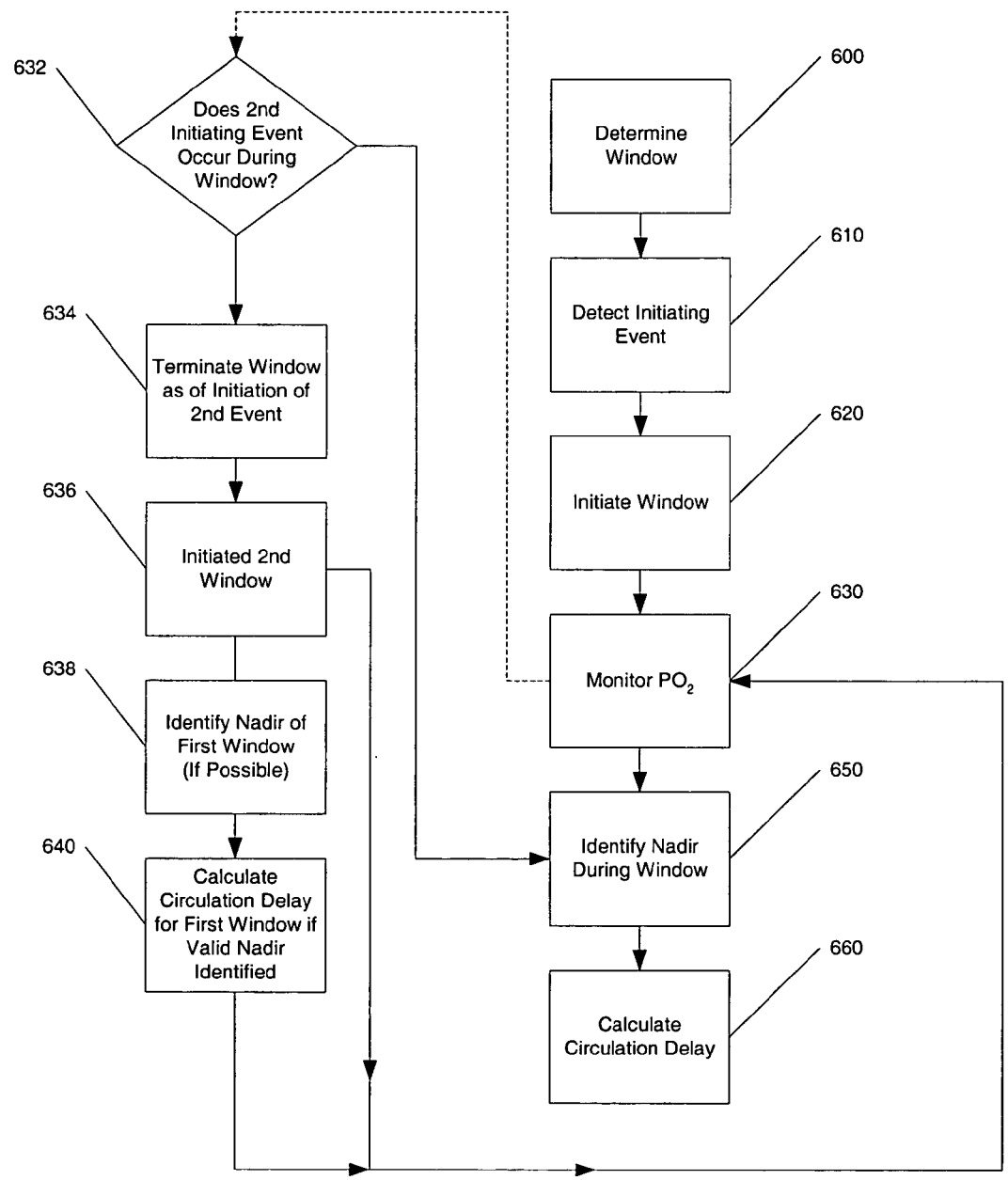
FIG. 11A is a flowchart illustrating a process for measuring circulation delay.

With the normal variations and fluctuations in respiration and oxygen saturation, identifying the initiating event and the nadir may pose a challenge. FIG. 11A is a flowchart that illustrates a process to identify these events and to calculate circulation delay. Initially, the patient's respiration is monitored to determine (600) an apnea/hyperventilation window ("window"). The determination may be based on a single episode or an average of a number of episodes over time. The window defines the period of time during which oxygen saturation measurements are considered relevant to circulation delay. As illustrated in FIGS. 1A and 1B, the window could begin at any point following the onset of the apnea and terminate concurrently with the termination of the hyperventilation.

In one embodiment, the window begins with the termination of the apnea and extends for the average measured duration of e.g., hyperventilation. More specifically, during this initial monitoring of the patient, an apnea is the trigger to denote a subsequent period of hyperventilation that is measured; as opposed to simply measuring or averaging periods of apparent hyperventilation that may be unassociated with an apnea. For example, normal respiration patterns may wax and wane and, depending upon classification parameters (e.g., a percentage change), could be sensed as hyperventilation. Likewise, other variables could lead to elevated respiration rates (dreaming, ambient temperature, body position, etc.) that should not be included.

Once the relevant window is defined, the circulation delay measurement process begins. Sensors monitor (610) for the appropriate indicating event. For example, the indicating event may be the termination of an apnea. As such, the onset of the apnea is an early indicator and when respiration resumes (i.e., termination of the apnea) the window is initiated (620).

During the duration of the window, oxygen saturation levels are evaluated (630). Monitoring of oxygen saturation levels outside of the window is optional. The point at which the lowest level of oxygen saturation occurred during the window is the nadir and is identified (650) as such and referenced to a timeline. Circulation delay is determined by calculating (660) the time interval between the initiating event (e.g., termination of apnea) and the nadir.

FIG. 11A also illustrates certain optional steps that may be taken subsequent to initiating the window (620) and monitoring $PO_2$. More specifically, after initiating a window based on a first event, the system continues to monitor (632) for any other "initiating" events (e.g., apnea). If no second initiating event occurs during the duration of the first window (620), then the process identifies the nadir (650) and continues as previously described.

If a second initiating event occurs and is sensed (632), then the first window is terminated (634) concurrent with the initiating event. Since the two events (e.g., apneas or apnea terminations) are "overlapping" during the first window, continuing the first window may gave spurious results since the second event will likely prolong a desaturation period. Furthermore, a nadir identified during the full first window may not be reflective of a response to the first event, but rather the second; thus, measured or calculated circulation delays could be inaccurate.

Within the truncated first window, it may still be possible to identify a representative or accurate nadir (638). To the extent that the nadir is simply the lowest value of oxygen saturation, then a nadir is always mathematically identifiable. However, as certain embodiments define the nadir as the low point followed by an approximately immediate increase, this event might not exist in the truncated first window. Furthermore, there may be additional reasons to disqualify the data from the truncated window. As such, if a meaningful nadir can be identified (638), that value is used to calculate circulation delay (640) for the first event. Regardless, the previously described process resumes at (630) for the second event and second window. Should a subsequent initiating event occur, the process repeats from (632).

As indicated, even when a nadir is mathematically identifiable, it is ignored in some cases. Whether for initial testing/diagnosis, monitoring, or performance evaluation, the obtained circulation delay should be sufficiently accurate. There are many reasons why spurious or anomalous values could be measured or sensed and one way to achieve the desired level of accuracy and reliability is to ignore or discard such values.

Figure 11B:
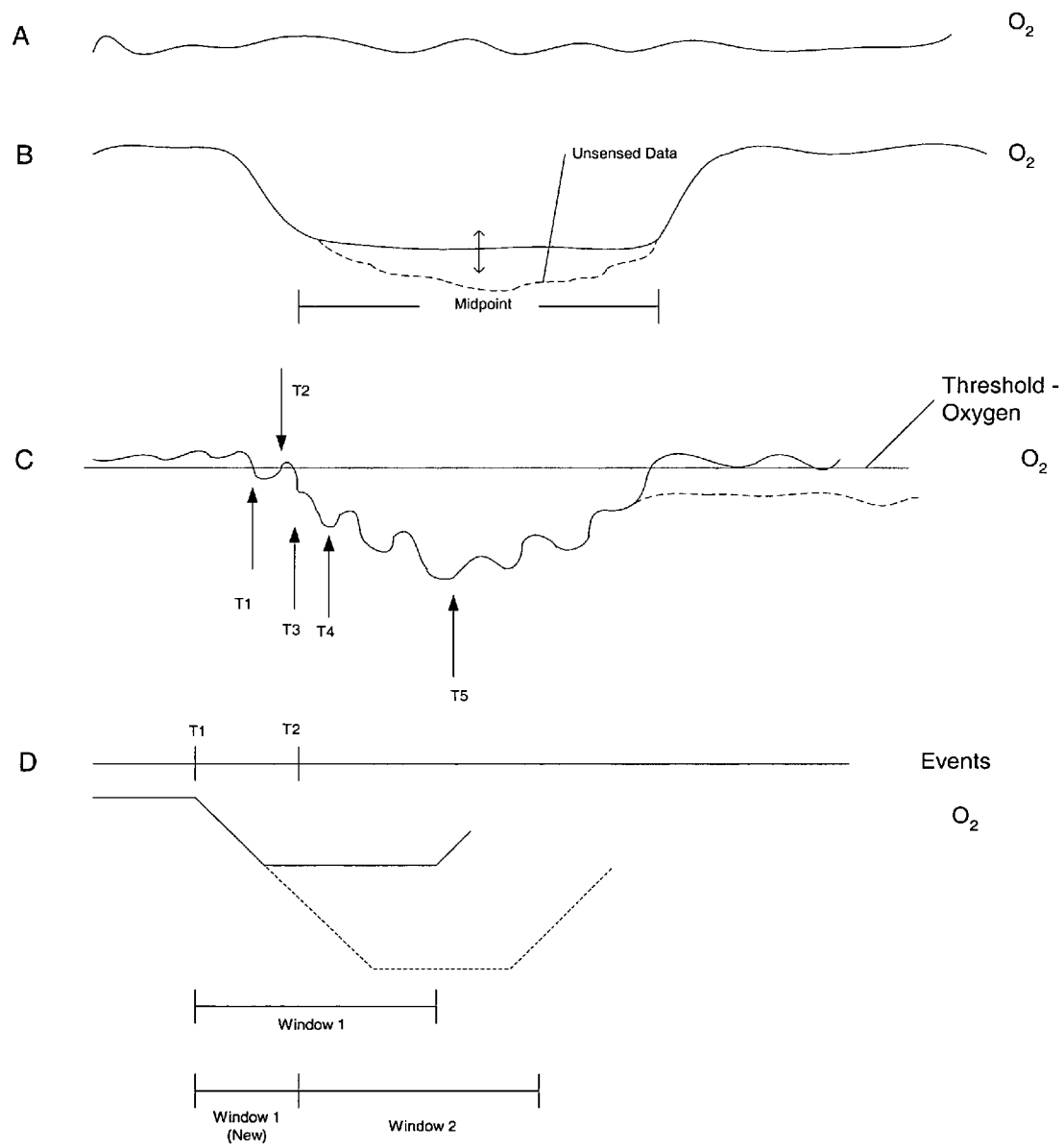
FIG. 11B is a schematic diagram illustrating processes for identifying events used to measure circulation delay in the flowchart of FIG. 11A.

FIG. 11B schematically illustrates various sensed oxygen saturation scenarios. Scenario A illustrates normal oxygen saturation values without any initiating events. As should be expected, oxygen saturation is not necessarily flat and may vary within normal ranges. Thus, during the segment illustrated a mathematical nadir could be identified and a nadir defined by a lowest point followed by a subsequent increase could also be identified. Of course, such a value is essentially meaningless in the present context. This simply indicates that the identified nadir must be identified relative to an event of interest and this is accomplished, in one embodiment, by defining the appropriate window.

Scenario B illustrates oxygen saturation in response to an event. As expected, the saturation values decrease substantially and eventually return to normal levels. As indicated by the solid line, the measured or sensed oxygen saturation essentially bottoms out for a prolonged period of time. When this occurs, the midpoint of this prolonged period of time is selected as labeled as the nadir. This is in opposition to the nadir as previously utilized wherein a subsequent local minimum followed by an almost immediate increase is required. Though an "increase" does occur at the end of this prolonged period of time, that point is not selected as the nadir, in this example, because it is assumed that the flat line levels are due to sensor inadequacies rather that oxygen saturation values holding steady at some sub-normal value. The actual oxygen saturation values during this prolonged period of time are indicated by the dotted line. Thus, selecting the midpoint serves as an averaging function. Of course, rather than making such assumptions, these types of readings could simply be discarded, which may result in a lower number of events that qualify for analysis.

Scenario C illustrates several additional concepts. Initially, oxygen saturation is generally not smooth and continuous, but rather includes numerous fluctuations. Thus, simply identifying any local minimum followed by an increase will typically be insufficient to identify the desired point. As such, the lowest measured point during the entire window that is followed by a proximate increase is the selected parameter, in certain embodiments.

Another screening parameter that may be employed is that any decrease below the threshold must exceed a predetermined value in order to be considered. For example, at time T1, PO$_2$, does drop below the threshold, reaches a local minimum and rises above the threshold at time T2. Assuming this was the lowest measured value during a window, it would be discarded since the value did not depart from the threshold by more than the predetermined amount. For example, certain embodiments require that PO$_2$ drop more than 3% below threshold to be considered valid. The particular values may be selected based upon a balance between desired accuracy and the inclusion of the maximum number of events.

Assuming an event occurs at T3, PO$_2$ begins to decline (no indication of transport delay is illustrated in this example). A local minimum occurs at T4 and simply illustrates that because PO2 continues to decline as a trend, the entire window must be evaluated before determining the nadir. Thus, the nadir is illustrated at time T5 as the lowest level during the window, followed by a subsequent increase. As time progresses, PO$_2$ rises and eventually exceeds the threshold, as indicated by the solid line. When this occurs, the data collected is considered valid and utilized. However, if PO$_2$ rises, but does not return sufficiently close to the threshold, as indicated by the dotted lines, then the data is considered invalid and discarded. That is, if levels do not return to a normalized range, the lower PO$_2$ might be due to issues other than the initiating event and would thus skew the data. Of course, if PO$_2$ levels remain low or become dangerously know, the system may take various steps to alert the patient, alert the caregiver or emergency services, and/or deliver an available therapy if appropriate.

In one embodiment, PO$_2$ levels should return to within approximately 2% of the threshold values to be considered valid. The time limit for this return may be set accordingly. For example, the system may require this return during the window. Alternatively, the time limit is correlated to the duration of the relevant event (e.g., apnea) or the duration of the relevant event plus some offset period.

The offset added to the time limit may optionally be used to either qualitatively assess collected data or may be used to exclude data. For example, if the return to threshold occurs within an amount of time equal to or less than the duration of the event, the data may be considered valid and of high quality. If the return occurs during an initial offset period (e.g., 4 seconds), the data may also be considered to be valid and of high quality. If a return occurs, but is in a secondary offset period (e.g., greater than 4 seconds in the above example, but less than a maximum value), then the data is considered, but denoted as being of a lower quality. If the levels do not return to the threshold values within the secondary offset periods, they may be excluded. As such, depending upon the timing and the desired degree of accuracy and/or reliability, various classifications may be imparted to quantify the value of the data.

Scenario D illustrates a situation where events (e.g., apneas) overlap during a given window. At time T1, the first event occurs and PO$_2$ begins to drop and at the same time window 1 is initiated. In this example, event duration and transport delay are not illustrated. The full duration of window 1 is illustrated. At time T2, a second event occurs. As previously explained, this terminates window 1, reducing it to window 1 (new). In addition, a new window 2 is initiated.

If oxygen saturation is represented by the solid line, then a potentially valid nadir is available during the window 1 (new). If represented by the dashed line, then oxygen saturation simply declines through the entirety of window 1 (new) and no useable data is available. As illustrated, if the original window 1 had been allowed to continue, the lowest value could be used as a nadir (assuming some subsequent increase were present during the window (e.g., scenario B), though not illustrated). This would be incorrect since window 1 is correlated to the first event that started at time T1 and the nadir is actually relevant to the second event of T2. Thus, circulation delay calculated for the first event would be incorrect in such scenario.

The process illustrated in FIGS. 11A and 11B may be implemented with an implanted system. For example, the oximeter (implanted or external) is communicatively coupled with and provides data to the IMD. The CD module within the IMD processes the information and determines circulation delay.

Figure 12:
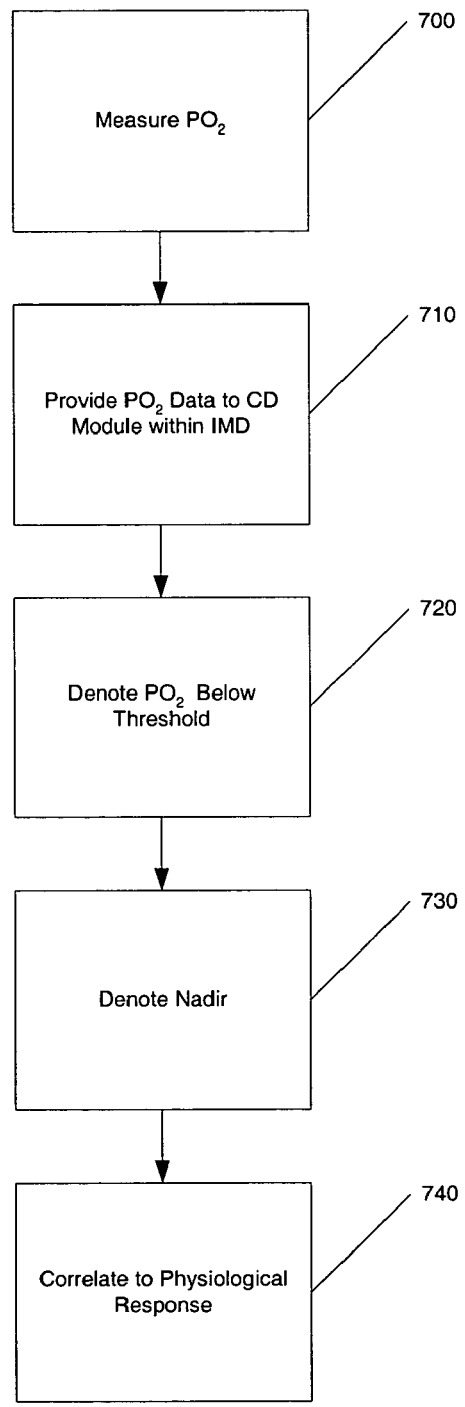
FIG. 12 is a flowchart illustrating a process of using oxygen saturation measurements to identify physiologic events.

In addition, the IMD receiving oxygen saturation levels from an internal or external oximeter provides a sensing platform for physiological events. Referring to FIG. 12, the oximeter measures (700) oxygen saturation levels and provides (710) this data to the appropriate processing component (e.g., the CD module) of the IMD. The IMD monitors PO$_2$ levels and identifies (720) points at which such levels drop below a predetermined threshold. Similarly, for any given period of time while below that threshold, the IMD identifies (730) the lowest point and can also identify when the level returns to or exceeds the threshold value. The timing and duration of these intervals is also provided to the IMD. This data is then correlated (740) to the physiological events that caused the variation in saturation levels. For example, a continual, prolonged drop in oxygen saturation denotes an apnea. Thus, the IMD and oximeter in combination may be used to sense apneas without respiratory data. Such data may have many additional uses, such as for example, initiating or controlling overdrive pacing or controlling or titrating external devices such as a CPAP machine.

In general, the measure of circulation delay has been described with reference to each event (e.g., apnea). As the effects of pacing may affect trends rather than specific events, it should be appreciated that such trends and/or averaged or collected data may be substituted for individual events. That is, measured circulation delay may be determined over a period of time. Furthermore, reduction in circulation delay may be determined based on averaged or collected values over a period of time. In addition, the therapy may be provided or some time (e.g., hours or days) before a reduction is determined.

Although the present invention has been described with reference to preferred embodiments, persons skilled in the art will recognize that changes may be made in form and detail without departing from the spirit and scope of the invention.

The invention claimed is:

1. An implantable medical device system comprising:
   an implantable pulse generator;
   a controller coupled with the implantable pulse generator and selectively providing pacing stimuli;
   an oximeter;
   a respiration sensor; and
   a circulation delay module communicatively coupled with the controller, the oximeter, and the respiration sensor and providing a measurement of circulation delay which is a time from a resumption of respiraton sensed by the respiration sensor to a nadir of oxygen saturation sensed by the oximeter, wherein the controller receives the measurment of circulation delay and selectively provides pacing based upon the measurement of circulation delay.

2. The implantable medical device system of claim 1, further comprising a housing including the implantable pulse generator, the controller, the oximeter and the circulation delay module.

3. The implantable medical device system of claim 1, wherein the oximeter is externally positioned and communicatively coupled with the circulation delay module via telemetry.

4. The implantable medical device system of claim 1, wherein the respiration sensor senses a termination of an apnea that initiates an observation window for the oximeter.

5. The implantable medical device system of claim 4, wherein the oximeter senses a lowest oxygen saturation point during the window and communicates that point to the circulation delay module.

6. The implantable medical device system of claim 1, wherein the controller initiates overdrive pacing if the measurement of circulation delay exceeds a predetermined threshold.

7. An implantable medical device system comprising:
   an implantable pulse generator;
   a controller coupled with the implantable pulse generator and selectively providing pacing stimuli;
   an oximeter;
   an apnea sensor configured to sense an onset and termination of an apnea event; and
   a circulation delay module communicatively coupled with the controller, the oximeter, and the apnea sensor and providing a measurement of circulation delay that is measured from either the onset of the apnea event as sensed by the apnea sensor to a perceived onset of the apnea event as sensed by the oximeter or the termination of the apnea event as sensed by the apnea sensor to a perceived termination of the apnea event as sensed by the oximeter, wherein the controller receives the measurement of circulation delay and selectively provides pacing based upon the measurement of circulation delay.

8. The implantable medical device system of claim 7, further comprising a housing including the implantable pulse generator, the controller, the oximeter and the circulation delay module.

9. The implantable medical device system of claim 7, wherein the oximeter is externally positioned and communicatively coupled with the circulation delay module via telemetry.

10. The implantable medical device system of claim 7, wherein the apnea sensor is a respiration sensor communicatively coupled with the circulation delay module.

11. The implantable medical device system of claim 10, wherein the respiration sensor senses a termination of an apnea that initiates an observation window for the oximeter.

12. The implantable medical device system of claim 11, wherein the oximeter senses a lowest oxygen saturation point during the window and communicates that point to the circulation delay module.

13. The implantable medical device system of claim 7 wherein the controller initiates overdrive pacing if the measurement of circulation delay exceeds a predetermined threshold.

* * * * *

UNITED STATES PATENT AND TRADEMARK OFFICE
CERTIFICATE OF CORRECTION

| | | |
|---|---|---|
| PATENT NO. | : 7,315,759 B2 | Page 1 of 1 |
| APPLICATION NO. | : 10/945639 | |
| DATED | : January 1, 2008 | |
| INVENTOR(S) | : Toby H. Markowitz et al. | |

It is certified that error appears in the above-identified patent and that said Letters Patent is hereby corrected as shown below:

Col. 16, line 1, delete "Saluration" and insert in place there of --Saturation--.

Signed and Sealed this

Thirteenth Day of January, 2009

JON W. DUDAS
*Director of the United States Patent and Trademark Office*